United States Patent
Schaefer et al.

(10) Patent No.: US 6,461,343 B1
(45) Date of Patent: Oct. 8, 2002

(54) DISPOSABLE ABSORBENT ARTICLE WITH FOLDED EAR PANELS AND METHOD OF MAKING SAME

(75) Inventors: Markus Robert Schaefer, Euskirchen (DE); Michael Thomas Huber, Cincinnati, OH (US); Josef Heinz Weber, Bad Muenstereifel (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/367,904

(22) PCT Filed: Feb. 18, 1997

(86) PCT No.: PCT/US97/02096

§ 371 (c)(1),
(2), (4) Date: Aug. 19, 1999

(87) PCT Pub. No.: WO98/35641

PCT Pub. Date: Aug. 20, 1998

(51) Int. Cl.[7] .................................................. A61F 13/15
(52) U.S. Cl. ................... 604/389; 604/391; 604/386; 604/394; 604/396
(58) Field of Search ............................ 604/389, 390, 604/391, 386, 396, 394; 428/40.1, 352, 261, 343, 354; 156/204, 269, 324

(56) References Cited

U.S. PATENT DOCUMENTS

| 3,930,502 A | 1/1976 | Tritsch | 128/287 |
|---|---|---|---|
| 4,084,592 A | 4/1978 | Tritsch | 128/287 |
| 4,237,890 A | * 12/1980 | Laplanche | 128/287 |
| 4,670,012 A | 6/1987 | Johnson | 604/390 |
| 5,591,521 A | * 1/1997 | Arakawa et al. | 428/352 |

FOREIGN PATENT DOCUMENTS

| DE | 34 40 544 A | 5/1986 |
|---|---|---|
| FR | 2 267 058 A | 11/1975 |
| WO | WO 84 04242 | 11/1984 |
| WO | WO 95 22951 | 8/1995 |
| WO | WO 95 35079 | 12/1995 |

* cited by examiner

Primary Examiner—Aaron J. Lewis
Assistant Examiner—Jacqueline F Stephens
(74) Attorney, Agent, or Firm—Michael S. Kolodesh; David M. Weirich; Steven W. Miller

(57) ABSTRACT

The present invention relates to a means of reproducibly and consistently folding the ear panels on disposable absorbent articles in order to simplify and accelerate the diaper opening process for the user, reduce the risk of potential injury to the end user and wearer caused by clipped ear panels, and create for packaging purposes, a more aesthetically satisfying arrangement in the disposable diaper pack. In another aspect of the invention, a method for the making of a disposable absorbent diaper, which incorporates the folding of the ear panels, is outlined.

3 Claims, 2 Drawing Sheets

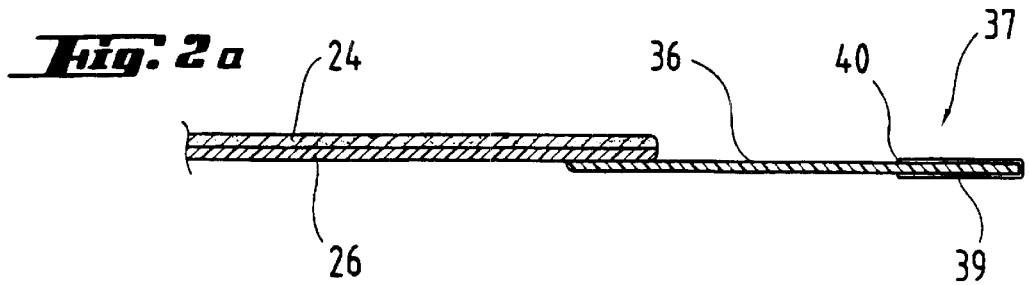
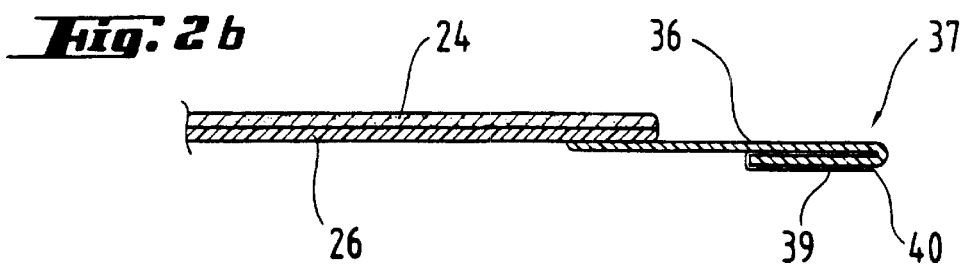
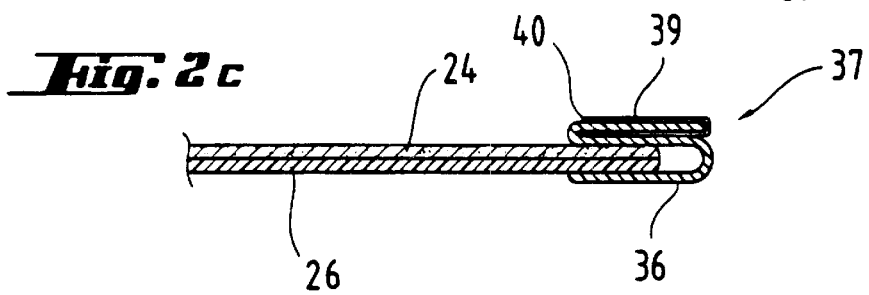
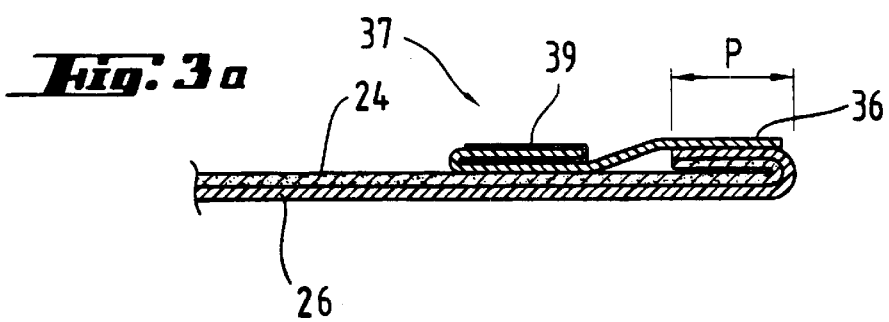
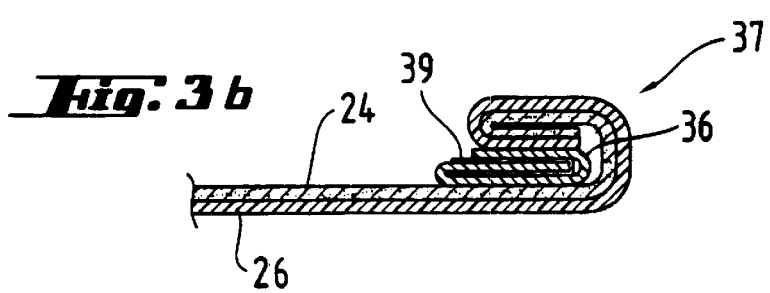

DISPOSABLE ABSORBENT ARTICLE WITH FOLDED EAR PANELS AND METHOD OF MAKING SAME

FIELD OF THE INVENTION

The present invention relates to a superior way of folding ear panels on disposable absorbent articles. In particular, attention is directed towards disposable diapers.

BACKGROUND OF THE INVENTION

Disposable absorbent articles, in particular, disposable diapers are well-known articles of manufacture that are designed to be worn principally by infants and incontinence sufferers. Such diapers are worn about the lower torso of the wearer and are intended to absorb and contain urine and other bodily discharges, thus preventing the soiling, wetting, or similar contamination of articles (for example, clothing, bedding, other persons, etc.) that may come into contact with such a diaper in use.

On reaching for a fresh disposable diaper, the user normally unfolds the diaper from the folded and packaged configuration into a semi-folded configuration, locates the ear panels furnished with the tape tab fastening devices and opens out the diaper into an unfolded configuration that permits the user to fit and fasten the diaper about the waist of the wearer to effect a side closure. In the folded and semi-folded configurations, the ear panels typically lie adjacent to the back waist region of the diaper resulting in the tape tab fastening devices being in a position that either does not facilitate easy user access or that poses a risk to the user and even the wearer due to the clipped nature of the ear panels. Clipping tends to occur during the manufacturing cutting phase as a result of the haphazard arrangement of the ear panels on the chassis assembly.

The prior art does not reveal any particularly pertinent information on the subject of the folding of ear panels on disposable absorbent articles such as diapers. For example, U.S. Pat. No. 3,863,637 focuses on the folding of a diaper. In particular, the diaper is longitudinally folded into a configuration which in cross-section resembles the Greek symbol sigma on one side of the longitudinal centreline of the diaper and a reverse sigma on the opposite side of the diaper. The diaper has a rectangular outline with adhesive strips being provided on the opposite corners of one end of the diaper. Due to the rectangular shape of the diaper, the issue of ear folding is simply not encountered. In contrast, U.S. Pat. No. 4,050,462 does mention the folding of ear panels. The document describes how a diaper according to the teachings of the invention can be folded and adapted for packaging. The foreshortening of the narrow crotch section as a result of the presence of elastics causes the diaper to fold itself transversely in half, thus enabling the outwardly extending ear panels at the edges of the waistband sections to be easily folded inwards. EP 0 452 951 B1 describes the folding of side sections on a training pants for the purposes of facilitating packaging. In particular, the document relates to a training pants having a front portion, a back portion and side sections connecting both portions together. The side sections extend from the waist opening to the respective leg openings and are folded along a centre line of the training pants extending in the longitudinal direction so that they are positioned between the front portion and the back portion of the training pants. Currently, other disposable diaper products on the market reveal a random arrangement in relation to the folding of ear panels and furthermore, clipped ear panels are very prevalent. This is most pronounced within the disposable diaper packs on opening.

As a result of the above prior art attempts, it has been recognised by those skilled in the art that it would be desirable to provide a means of reproducibly and consistently folding the ear panels on disposable diapers in order to simplify and accelerate the diaper opening process for the user, reduce the risk of potential injury to the end user and wearer caused by clipped ear panels, and create for packaging purposes, a more aesthetically satisfying arrangement in the disposable diaper pack. The solution is found to be ear panels that are multiply folded to create a configuration that exposes the tape tab fastening devices of the ear panels to the user when the diaper has been opened into the semi-folded configuration and that reveals no clipped ears.

It has now been discovered that the benefits of the present invention range from an easy one step opening action for the diaper and the tape tab fastening device; to a product with a superior and enhanced appearance due to the neat, controlled and consistent manner of the ear panel folding; to a product that is extremely user friendly and that causes no harm either to the user or to the wearer; to a product that confers a high level of user satisfaction and confidence; and to an arrangement that is most attractive on first impact when the user opens a disposable diaper pack to obtain a diaper. Furthermore, the inclusion of the folding procedure on current manufacturing lines is straightforward. In fact, the folding procedure results in increased reliability, process simplification and permits the elimination of the use of static charging equipment, which poses a safety risk to operators.

SUMMARY OF THE INVENTION

In one aspect of the present invention, a disposable absorbent article having a front waist region and a back waist region, a chassis assembly comprising a liquid pervious topsheet and a liquid impervious backsheet joined with the topsheet; an absorbent core positioned between the topsheet and the backsheet; and a pair of ear panels in the back waist region is disclosed. The ear panels comprise a tape tab fastening device comprising an attachment area and a functional area. Each of the ear panels is folded backwards onto itself to at least the width of the attachment area of the tape tab fastening device and subsequently is folded forward onto itself to at least once the width of the attachment area of the tape tab fastening device. The portion of the ear panel after forward folding not comprising the attachment area of the tape tab fastening device is disposed in a configuration partially overlapping the attachment area of the tape tab fastening device. In a preferred embodiment of the present invention, each of the ear panels is folded forward onto itself to twice the width of the attachment area of the tape tab fastening device. The ear panels can be either unitary with the back waist region of the diaper or joined along a line of juncture to same.

In another aspect of the present invention, a method of making a disposable diaper with the features described above is disclosed. The steps comprise providing a disposable diaper; folding each of the ear panels backwards onto itself to at least the width of the attachment area of the tape tab fastening device; folding each of the ear panels forward onto itself to at least once the width of the attachment area of the tape tab fastening device; folding each portion of the ear panels after forward folding not comprising the attachment area of the tape tab fastening device into a configuration that partially overlaps the attachment area of the tape tab fastening device. In another preferred embodiment of the present invention, the ear panels are joined along a line of juncture to the back waist region before the forward folding step occurs.

BRIEF DESCRIPTION OF THE DRAWINGS

It is believed that the invention will be better understood from the foregoing description in conjunction with the accompanying drawings in which:

FIG. 2a is a cross-sectional view through line A—A in FIG. 1 of the preferred disposable diaper embodiment;

FIG. 2b is a continuation from FIG. 2a after the ear panel has been folded backward onto itself;

FIG. 2c is a continuation from FIG. 2b after the ear panel has been folded forwarded onto itself to at least once the width of the attachment area of the fastening device;

FIG. 3a is a preferred embodiment of the present invention and is a continuation from FIG. 2c. In this embodiment, the ear panel has been folded forwarded onto itself to twice the width of the attachment area of the tape tab fastening device.

FIG. 3b is a continuation from FIG. 3a and shows the fully folded configuration of the ear panel.

DETAILED DESCRIPTION OF THE INVENTION

Figure 1:
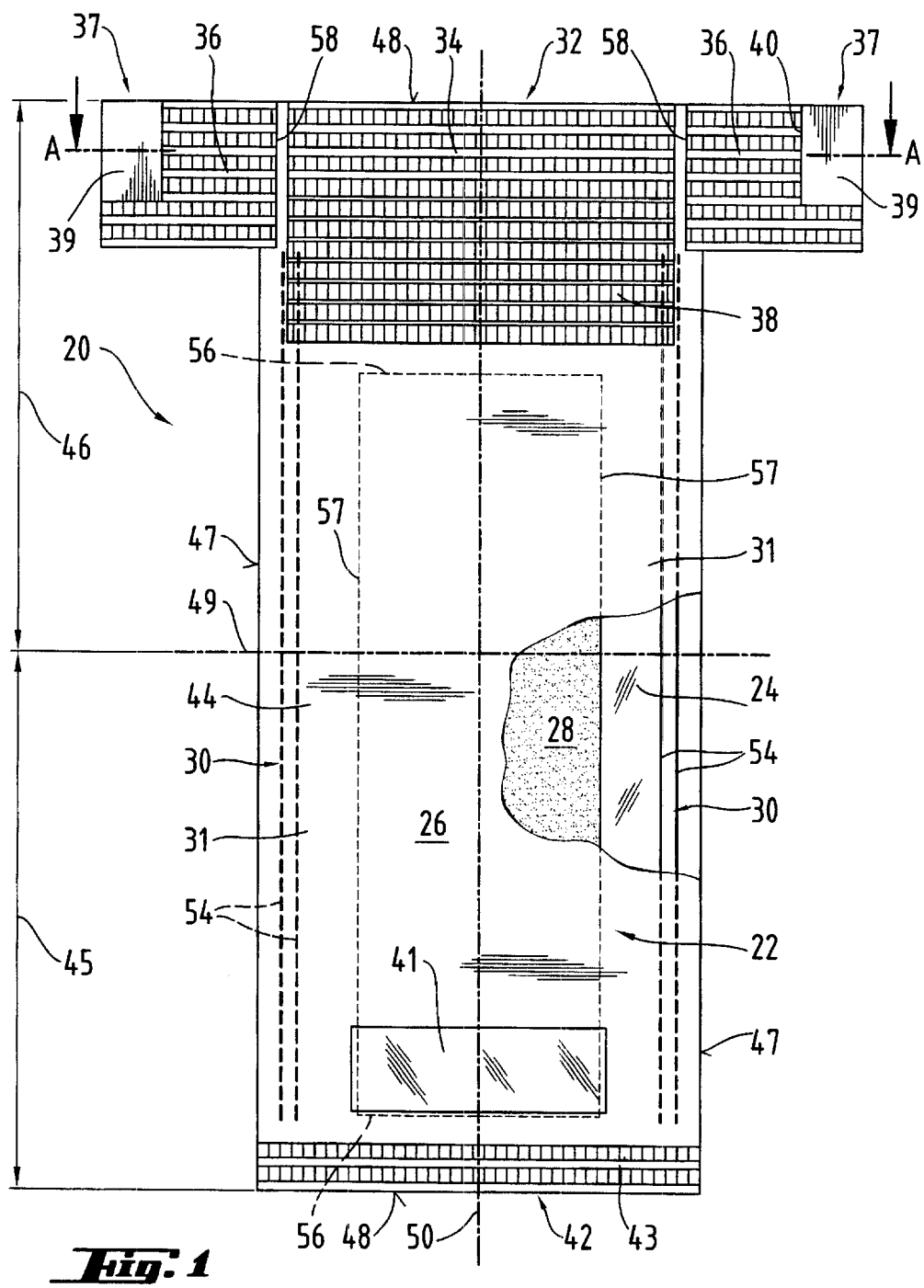
FIG. 1 is a plan view of a disposable diaper embodiment of the present invention having portions cut away to reveal the underlying structure with the outer surface of the diaper facing the viewer.

As used herein, the term "disposable absorbent article" refers to articles which absorb and contain body exudates; and more specifically, refers to articles which are placed against or in proximity to the body of the wearer to absorb and contain the various exudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer. The term "panel" is used herein to denote an area or element of the waist feature or the diaper. (While a panel is typically a distinct area or element, a panel may overlap somewhat with an adjacent panel.) As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element.

FIG. 1 is a plan view of the diaper 20 of the present invention in its flatout, uncontracted state (i.e., with elastic induced contraction pulled out) with portions of the structure being cut away to more clearly show the construction of the diaper 20 and with the portion of the diaper 20 that faces away from the wearer, the outer surface, facing the viewer. As shown in FIG. 1, the diaper 20 has a generally "T-shape" and comprises a chassis assembly 22 comprising a liquid pervious topsheet 24, a liquid impervious backsheet 26 joined with the topsheet 24, an absorbent core 28 positioned between the topsheet 24 and the backsheet 26; extensible leg cuffs 30 each comprising a leg flap panel 31 and one or more elastic members, elastic strands 54, operatively joined with the leg flap panel 31; an extensible back waist feature 32 comprising a central waistband panel 34, a pair of ear panels 36, each comprising a tape tab fastening device 37, and a hip panel 38; a landing member for tape tab fastening device 37; and an extensible front waist feature 42 comprising a front waist panel 43.

Each of the panels may be a separate member joined to the overall diaper structure or may be unitary with the diaper 20 in that they comprise an extension of other elements of the diaper such as the topsheet 24, the backsheet 26, or both. In the embodiment shown in FIG. 1, all of the panels except for the ear panels 36 comprise an extension of the topsheet 24 and the backsheet 26. The ear panels 36 comprise a separate member joined to the central waistband panel 34 and at least a portion of the hip panel 38. Further, any or all of the panels may be extensible. The chassis panel 22 is typically not extensible in order to maintain the integrity of the absorbent core 28 during use, although it may be rendered extensible such as by being formed as a structural elastic-like film (SELF) web as described herein. Preferably, the extensible panels comprise a SELF web. The use of a SELF web allows the force/extension properties of each of the panels to be specifically designed to maximise the fit and containment of the diaper with a minimum amount of materials (no conventional elastic materials are needed).

As is evident from FIG. 1, the diaper 20 is provided with a closure system comprising a tape tab fastening device 37 and a landing member 41 for fitting the diaper 20 on the wearer. The tape tab fastening device 37 comprises an attachment area 39 and a functional area (not shown), and the landing member, is preferably a reinforcing strip 41 or, the alternative, a portion of the backsheet 26, positioned in the front waist region 45 of the diaper 20. The attachment area 39 is the area on the tape tab fastening device 37 that is joined to the ear panel 36 and the functional area is the area on the tape tab fastening device 37 on which functional elements are located to permit engagement with the landing member on the front waist region 45 of the diaper. The functional elements may take on a number of configurations such as adhesive fastening elements, mechanical fastening elements, a combination of adhesive fastening elements and mechanical fastening elements, or any other means as are known to the man skilled in the art.

The diaper 20 of FIG. 1 has an inner surface (not shown), an outer surface 44 (facing the viewer in FIG. 1) opposed to the inner surface, a front waist region 45, a back waist region 46 opposed to the front waist region 45, and a periphery which is defined by the outer edges of the diaper 20 in which the longitudinal edges are designated 47 and the end edges are designated 48. (While the man skilled in the art will recognise that a diaper is usually described in terms of having a pair of waist regions and a crotch region between the waist regions; in this application, for simplicity of terminology, the diaper 20 is described as having only waist regions, each of the waist regions including a portion of the diaper which would typically be designated as part of the crotch region). The inner surface of the diaper 20 comprises that portion of the diaper 20 which is positioned adjacent to the body of the wearer during use (i.e., the inner surface generally is formed by at least a portion of the topsheet 24 and other components joined to the topsheet 24). The outer surface 44 comprises that portion of the diaper 20 which is positioned away from the body of the wearer (i.e., the outer surface 44 generally is formed by at least a portion of the backsheet 26 and other components joined to the backsheet 26). The front waist region 45 and the back waist region 46 extend, respectively, from the end edges 48 of the periphery to the lateral centreline 49 of the diaper 20. (The lateral direction (x direction or width) is defined as the direction parallel to the lateral centreline 49 of the diaper 20; the longitudinal direction (y direction or length) being defined as the direction parallel to the longitudinal centreline 50; and the axial direction (z direction or thickness) being defined as the direction extending through the thickness of the diaper 20.)

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form certain of the panels and portions of the periphery of the diaper. The periphery defines the outer perimeter or, in other words, the edges of the diaper 20. The periphery comprises the longitudinal edges 47 and the end edges 48.

The chassis assembly 22 (chassis panel) of the diaper 20 is shown in FIG. 1 as comprising the main body (chassis) of the diaper 20. The chassis assembly 22 comprises at least an absorbent core 28, preferably an outer covering layer comprising the topsheet 24 and the backsheet 26. Thus, the chassis assembly 22 comprises the main structure of the diaper with other features added to form the composite diaper structure. An exemplary example of a chassis assembly of the present invention is described in U.S. Pat. No. 3,860,003.

The absorbent core 28 may be any absorbent means which is capable of absorbing and retaining liquids such as urine and other certain body exudates. The absorbent core 28 has a garment surface, a body surface, side edges 57, and waist edges 56. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. An absorbent structure useful as the absorbent core 28 of the present invention that has achieved wide acceptance and commercial success is described in U.S. Pat. No. 4,610,678. U.S. Pat. Nos. 4,673,402; 4,888,231; 5,147,345; 5,102,597; and 4,834,735; also describe absorbent structures that are useful in the present invention. The absorbent core 28 is preferably the dual-layer absorbent structure described in U.S. Pat. No. 5,234,423.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986. An exemplary attachment means of an open pattern network of filaments comprises several lines of adhesive filaments swirled into a spiral pattern such as is illustrated by the apparatus and methods shown in U.S. Pat. Nos. 3,911,173; 4,785,996; and 4,842,666. Alternatively, the attachment means may comprise heat bonds, pressure bonds, heat/pressure bonds, ultrasonic bonds, dynamic mechanical bonds, or any other suitable attachment means or combinations of these attachment means as are known in the art. The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 millimeters to about 0.051 millimeters. The backsheet 26 preferably comprises a polyethylene blend film of about 0.025 millimeters as is manufactured by Tredegar Corporation of Terre Haute, Id. and marketed as P8863.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by the attachment means (not shown). The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibres (e.g., wood or cotton fibres), synthetic fibres (e.g., polyester or polypropylene fibres), or a combination of natural and synthetic fibres. Preferably, the topsheet 24 is made of a hydrophobic material to isolate the wearer's skin from liquids which have passed through the topsheet and are contained in the absorbent core 28 (i.e., to prevent rewet). If the topsheet 24 is made of a hydrophobic material, at least the upper surface thereof is treated to be hydrophilic so that liquids will transfer through the topsheet 24 more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the material with the surfactant and immersing the material in the surfactant. A more detailed discussion of such a treatment and hydrophilicity is contained in U.S. Pat. No. 4,988,344.

The diaper 20 preferably further comprises extensible leg cuffs 30 for providing improved containment of liquids and other body exudates. Each extensible leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 describes a disposable diaper which provides a contractible leg opening having a leg flap and one or more elastic members to provide an elasticized leg cuff (gasketing cuff). U.S. Pat. No. 4,909,803, describes a disposable diaper having "stand-up" elasticized flaps (barrier cuffs) to improve the containment of the leg regions. U.S. Pat. No. 4,695,278 describes a disposable diaper having dual cuffs including a gasketing cuff and a barrier cuff. U.S. Pat. No. 4,704,115 discloses a disposable diaper or incontinent garment having side-edge-leakage-guard gutters configured to contain free liquids within the garment. U.S. Pat. No. 5,032,120 discloses an absorbent article having leg cuffs having a relatively low ultimate contact force at relatively high elongations accomplished, for example, by low contact force differential material. U.S. Pat. No. 5,087,255 discloses an absorbent article having inflected barrier cuffs with the distal edge positioned outboard of the proximal edge in one waist region and inboard in the other to provide better fit about the hips/buttocks. While each extensible leg cuff 30 may be configured so as to be similar to any of the leg bands, leg flaps, barrier cuffs, or elastic cuffs described above, as shown in FIG. 1, each extensible leg cuff 30 comprises the leg flap panel 31 extending laterally outwardly from the chassis panel 22, the side edge 57 of the absorbent core 28, and one or more elastic members, elastic strands 54, operatively joined with the leg flap panel 31, such as is described in U.S. Pat. No. 3,860,003.

The diaper 20 further comprises extensible waist features that provide improved fit and containment. The extensible waist features at least extend longitudinally outwardly from the chassis assembly, preferably a respective waist edge 56 of the absorbent core 28, and generally form at least a portion of the end edge 48 of the diaper 20. Thus, in the embodiment shown in FIG. 1, the extensible back waist feature 32 comprises that portion of the diaper 20 extending from the waist edge 56 of the absorbent core 28 in the back waist region 46 to the end edge 48 of the diaper 20. While a disposable diaper 20 of the present invention is constructed with an extensible waist feature disposed in each waist region (an extensible back waist feature 32 and an extensible front waist feature 42), the discussion will focus on diapers having different configurations for each extensible waist feature. At a minimum, it is preferred that the diaper 20 have at least one of the extensible waist features constructed according to the present invention, more preferably at least the back extensible waist feature 32. The waist features can be constructed as a separate element joined to the chassis assembly 22 or as an extension of other elements of the diaper (i.e., unitary). The waist features will be described with respect to preferred embodiments in which certain portions or panels comprise an extension of other elements of the diaper such as the backsheet 26, the topsheet 24, or both, and other portions or panels comprise a separate element joined to other portions or panels of the waist feature or other panels of the diaper.

The extensible back waist feature 32 provides an extensible member that provides a more comfortable and contouring fit by initially conformably fitting the diaper to the wearer and sustaining this fit throughout the time of wear well past when the diaper has been loaded with exudates since the extensible back waist feature 32 allows the diaper to expand and, preferably, to contract. Further, the extensible back waist feature 32 develops and maintains wearing forces (tensions) that enhance the tensions developed and maintained by the closure system to maintain the diaper on the wearer and that enhance the fit of the diaper about the waist of the wearer. The extensible back waist feature 32 further provides more effective application of the diaper since even if the diaperer pulls one side (ear panel 36) of the extensible back waist feature 32 farther than the other during application (asymmetrically), the diaper will "self-adjust" during wear. As shown in FIG. 1, the extensible back waist feature 32 comprises a central waistband panel 34; a pair of ear panels 36; and a hip panel 38. In the embodiment shown in FIG. 1, the hip panel 38 is disposed longitudinally outwardly from the chassis assembly 22 (the chassis panel), preferably from the waist edge 56 of the absorbent core 28, in the middle zone of the back waist region 46; the central waistband panel 34 is disposed longitudinally outwardly from the hip panel 38; and the side panels 36 are each disposed laterally outwardly from the central waistband panel 34 and at least a portion of the hip panel 38. As discussed hereinafter, the particular positioning of each panel of the back waist feature is important to the overall functioning of the back waist feature.

The ear panels 36 are those portions of the extensible back waist feature 32 that extend laterally outwardly from the central waistband panel 34 and at least a portion of the hip panel 38. The ear panels 36 are each an extensible member that primarily function to provide a more comfortable and contouring fit by initially conformably fitting the diaper 20 to the wearer at application and sustaining this fit throughout the time of wear well past when the diaper 20 has been loaded with exudates by enlarging the circumference of the diaper 20 at the sides, attaching the back waist region 46 to the front waist region 45 of the diaper 20 to complete a closure for the diaper 20, and distributing forces along both the waist and legs to transfer these forces such that there is a snug fit with no skin irritation due to excessive forces on the legs or the waist. The ear panels 36 provide stretch as well as, in preferred embodiments, a contractive force after extension and application. Thus, the ear panels 36 provide a more comfortable and contouring fit by allowing the sides of the diaper to expand and contract. The ear panels 36 also develop and maintain wearing forces (tensions) and enhance the tensions developed and maintained by the tape tab fastening device 37 and landing member to maintain the diaper 20 on the wearer and enhance the fit. The ear panels 36 assist in maintaining the primary line of tension formed by the primary fastening system; allowing the diaper to conformably fit over the hips of the wearer where there is dynamic motion, and initially pretensioning the front extensible waist feature, if provided on the diaper 20, since the diaperer 20 typically stretches the ear panels 36 when applying the diaper on the wearer so that when the ear panels 36 contract, tension is transmitted from the ear panels 36 through the tape tab fastening device 37 and landing member 41 into the extensible front waist feature 42. The ear panels 36 further provide more effective application of the diaper 20 since even if the user pulls one ear panel 36 farther than the other during application, the diaper 20 will "self-adjust" during wear.

The ear panels 36 may have a number of different sizes and shapes. For example, the ear panels 36 may each have an arcuate shape so that forces transmitted through the ear panel 36 are along a line or zone disposed at an angle to the body of the wearer to fit the diaper into the lumbar curve of the back and to allow the tensional forces (the primary line of tension) to be directed downward toward the abdominal crease of the wearer so as to provide a continuous primary line of tension. Examples of such side panels are described in U.S. patent application Ser. No. 08/072,300; and U.S. patent application Ser. No. 08/155,048. The ear panels 36 have a rectangular shape in FIG. 1. For a typical "large" (8 kg to 14 kg) baby diaper, the ear panels 36 may, for example, have a size of about 63 mm in the lateral direction by about 57 mm in the longitudinal direction.

The ear panels 36 may be constructed in a number of configurations and from a number of different materials. Examples of diapers with elasticized side panels are disclosed in U.S. Pat. Nos. 4,857,067; 4,381,781; 4,938,753; and 5,151,091. Thus, the ear panels 36 may comprise conventional elastic materials or mechanically stretched laminates such as a zero strain stretch laminate or a SELF web. The ear panels 36 may comprise a separate element affixed to the back waist feature 32 at the central waistband panel 34 and the hip panel 38, or can be constructed as an extension of other elements of the back waist feature 32 or the diaper 20 such as the backsheet 26 or the topsheet 24, preferably both the topsheet 24 and the backsheet 26. In the embodiment of the present invention shown in FIG. 1, the ear panels 36 each comprise a separate SELF web joined to the back waist feature 32 (the central waistband panel 34 and the hip panel 38). The SELF web of the ear panels 36 preferably comprises a laminate of two or more layers, preferably two layers; most preferably a laminate of a layer of a polyethylene blend film such as is marketed by Clopay Corporation of Cincinnati, Ohio as Clopay 1401 and a nonwoven web such as P-8 material.

FIG. 2a is a cross sectional view through line A—A in FIG. 1 of the preferred disposable diaper embodiment. In more detail, FIG. 2a shows only a portion of the topsheet 24, a portion of the backsheet 26, an ear panel 36 and a tape tab fastening device 37. The attachment area 39 of the tape tab fastening device 37 is visible. In the embodiment shown in FIG. 2a, the ear panel 36 is joined to and extends laterally outwards from the back waist region 46. In FIG. 2a, the ear panel 36 is joined to the backsheet 26, but may equally be joined to the topsheet 24. The ear panel 36 may equally be a unitary part of the disposable diaper 20. FIG. 2b is a continuation from FIG. 2a. The ear panel 36 is folded backwards onto itself to at least the width of the attachment area 39 of the tape tab fastening device 37. The edge 40 of the attachment area 39 of the tape tab fastening device 37 can serve as a useful reference line for folding. During the process, knife welds (not shown) hold the folded ear panels 36 in place until the disposable diaper 20 has been packaged. In FIG. 2c, the ear panel 36 is subsequently folded forward onto itself to at least once the width of the attachment area 39 of the tape tab fastening device 37.

FIG. 3a is a preferred embodiment of the present invention and is a continuation from FIG. 2c. In this preferred embodiment, the ear panel 36 is folded forwarded onto itself to twice the width of the attachment area 39 of the tape tab fastening device 37. FIG. 3b is a continuation from FIG. 3a and shows the fully folded configuration of the ear panel 36, as desired by the present invention. In particular, the portion P of the ear panel 36 after forward folding not comprising the attachment area 39 of the tape tab fastening device 37 is disposed in a configuration partially overlapping the attachment area 39 of the tape tab fastening device 37. In another preferred embodiment of the present invention, each of the ear panels 36 is joined along a line of juncture to the back waist region 46. This is apparent from FIG. 1.

In another aspect of the present invention, the making of a disposable diaper 20 is disclosed. FIGS. 1, 2a, 2b, 2c, 3a and 3b are relevant. The method comprises the steps of (a) providing a diaper 20 comprising a front waist region 45 and a back waist region 46, a chassis assembly 22 comprising a liquid pervious topsheet 24 and a liquid impervious backsheet 26 joined to the topsheet 24; an absorbent core 28 positioned between the topsheet 24 and the backsheet 26; and a pair of ear panels 36 in the back waist region 46, the ear panels 36 comprising a tape tab fastening device 37 comprising an attachment area 39 and a functional area (not shown); (b) folding each of the ear panels 36 backwards onto itself to at least the width of the attachment area 39 of the tape tab fastening device 37; (c) folding each of the ear panels 36 forward onto itself to at least once the width of the attachment area 39 of the tape tab fastening device 37; (d) folding each portion of the ear panels 36 after forward folding not comprising the attachment area 39 of the tape tab fastening device 37 into a configuration that partially overlaps the attachment area 39 of the tape tab fastening device 37. In a preferred embodiment of the method, step (c) includes folding each of the ear panels 36 forward onto itself to twice the width of the attachment area 39 of the tape tab fastening device 37. In another preferred embodiment of the present invention, the ear panels 36 each comprise a web joined to the back waist feature 32 and step (b) occurs before the joining of the ear panels 36 to the back waist region 46 of the diaper 20 at a line of juncture 58. As used herein, the term "juncture" refers to regions where panels extend from or are joined to the chassis assembly 22. These regions can be any of various curved or straight lines, but they are not limited to lines. Thus, these regions can comprise flanges, strips, intermittent lines and the like.

What is claimed is:

1. Method of making a disposable diaper (20) wherein said method comprises the steps of:

(a) providing a disposable diaper (20) comprising a front waist region (45) and a back waist region (46), a chassis assembly (22) comprising a liquid pervious topsheet (24) and a liquid impervious backsheet (26) joined to said topsheet (24); an absorbent core (28) positioned between said topsheet (24) and said backsheet (26); and a pair of ear panels (36) in said back waist region (46), said ear panels (36) comprising a tape tab fastening device (37) comprising an attachment area (39) and a functional area;

(b) folding each of said ear panels (36) backwards onto itself to at least said width of said attachment area (39) of said tape tab fastening device (37);

(c) folding each of said ear panels (36) forward onto itself to at least once said width of said attachment area (39) of said tape tab fastening device (37);

(d) folding each portion (P) of said ear panels (36) after forward folding not comprising said attachment area (39) of said tape tab fastening device (37) into a configuration that partially overlaps said attachment area (39) of said tape tab fastening device (37).

2. Method according to claim 1 wherein said step (c) includes folding each of said ear panels (36) forward onto itself to twice said width of said attachment area (39) of said tape tab fastening device (37).

3. Method according to claim 2 wherein step (b) occurs before joining of said ear panels (36) to said back waist region (46) at a line of juncture (58).

* * * * *

UNITED STATES PATENT AND TRADEMARK OFFICE
CERTIFICATE OF CORRECTION

PATENT NO. : 6,461,343 B1
DATED : October 8, 2002
INVENTOR(S) : Schaefer et al.

It is certified that error appears in the above-identified patent and that said Letters Patent is hereby corrected as shown below:

Column 3,
Line 55, delete "flatout" and insert -- flat-out --.

Column 10,
Line 46, after "39", insert -- having a width --.

Signed and Sealed this

Fifteenth Day of June, 2004

JON W. DUDAS
*Acting Director of the United States Patent and Trademark Office*